(12) United States Patent
Rivero et al.

(10) Patent No.: US 7,429,384 B2
(45) Date of Patent: Sep. 30, 2008

(54) CHIMERIC ANTAGONIST ANTH1

(75) Inventors: Iraldo Bello Rivero, La Habana (CU); Yeny Torres Ruiz, La Habana (CU); Elizabeth Blanco Garcés, La Habana (CU); Giselle Pentón Roll, La Habana (CU); Pedro López Saura, La Habana (CU)

(73) Assignee: Centro de Ingenieria Genetica y Biotecnologia, C. Habana (CU)

( * ) Notice: Subject to any disclaimer, the term of this patent is extended or adjusted under 35 U.S.C. 154(b) by 99 days.

(21) Appl. No.: 10/513,931

(22) PCT Filed: May 8, 2003

(86) PCT No.: PCT/CU03/00006

§ 371 (c)(1),
(2), (4) Date: Apr. 11, 2005

(87) PCT Pub. No.: WO03/095488

PCT Pub. Date: Nov. 20, 2003

(65) Prior Publication Data

US 2006/0073115 A1    Apr. 6, 2006

(30) Foreign Application Priority Data

May 10, 2002    (CU) .................................. 2002/0095

(51) Int. Cl.
*A61K 39/00* (2006.01)
*A61K 45/00* (2006.01)
*A61K 38/21* (2006.01)
*C07K 14/00* (2006.01)
*A01N 37/18* (2006.01)

(52) U.S. Cl. .................. 424/198.1; 424/85.1; 424/85.2; 424/85.5; 424/192.1; 530/351; 514/2

(58) Field of Classification Search ....................... None
See application file for complete search history.

(56) References Cited

U.S. PATENT DOCUMENTS 5,073,627 A    12/1991    Cosman et al.

FOREIGN PATENT DOCUMENTS

| EP | 0 393 502 A | 10/1990 |
| EP | 0 614 981 A | 9/1994 |
| EP | 0 621 338 A | 10/1994 |
| WO | WO 94 21282 A | 9/1994 |

OTHER PUBLICATIONS

Fischer M, et al. A bioactive designer cytokine for human hematopoietic progenitor cell expansion. 1997. Nature Biotechnology. vol. 15, No. 2, pp. 142-145.*
Mickle J.E. et al. Genotype-phenotype relationships in cystic fibrosis. Med. Clin. N. Am. 2000. vol. 84, pp. 597-607.*
Starnes H.F. et al. Anti-IL-6 monoclonal antibodies protect against lethal *Escherichia coli* infection and lethal tumor necrosis factor-a challenge in mice. J. Immunol. 1990. vol. 145, pp. 4185-4191.*
Doherty G.M. et al. Evidence for IFN-g as a mediator of the lethality of endotoxin and tumor necrosis factor-a. J. Immunol. 1992. vol. 149, pp. 1666-1670.*
Bello, Y., et al., "The IFN-gamma pathophysiology. The role of soluble IFN-gamma-R alpha chain", *Biotecnologia Aplicada* 1995, 12(3):163-164.

* cited by examiner

*Primary Examiner*—Robert Landsman
*Assistant Examiner*—Bruce D. Hisong
(74) *Attorney, Agent, or Firm*—Hoffman & Baron, LLP

(57) ABSTRACT

A recombinant chimeric antagonist formed by a 60 amino acid fragment of the N-terminal region of human interleukin 2 (IL-2) fused to the N-terminal of the extracellular region of the alpha subunit of the gamma IFN (IFN γ) receptor. In vitro this protein has a T cell growth stimulating activity, it inhibits the growth stimulating activity of IL-2 in T cells, it inhibits the induction of HLA-DR by IFN γ and it inhibits the antiproliferative activity of γ IFN. This invention can be applied in the field of medicine for the treatment of several pathologies such as autoimmune diseases, graft rejections, chronic inflammations, sepsis, ischemia and reperfusion syndrome and atherosclerosis.

Figure 1:
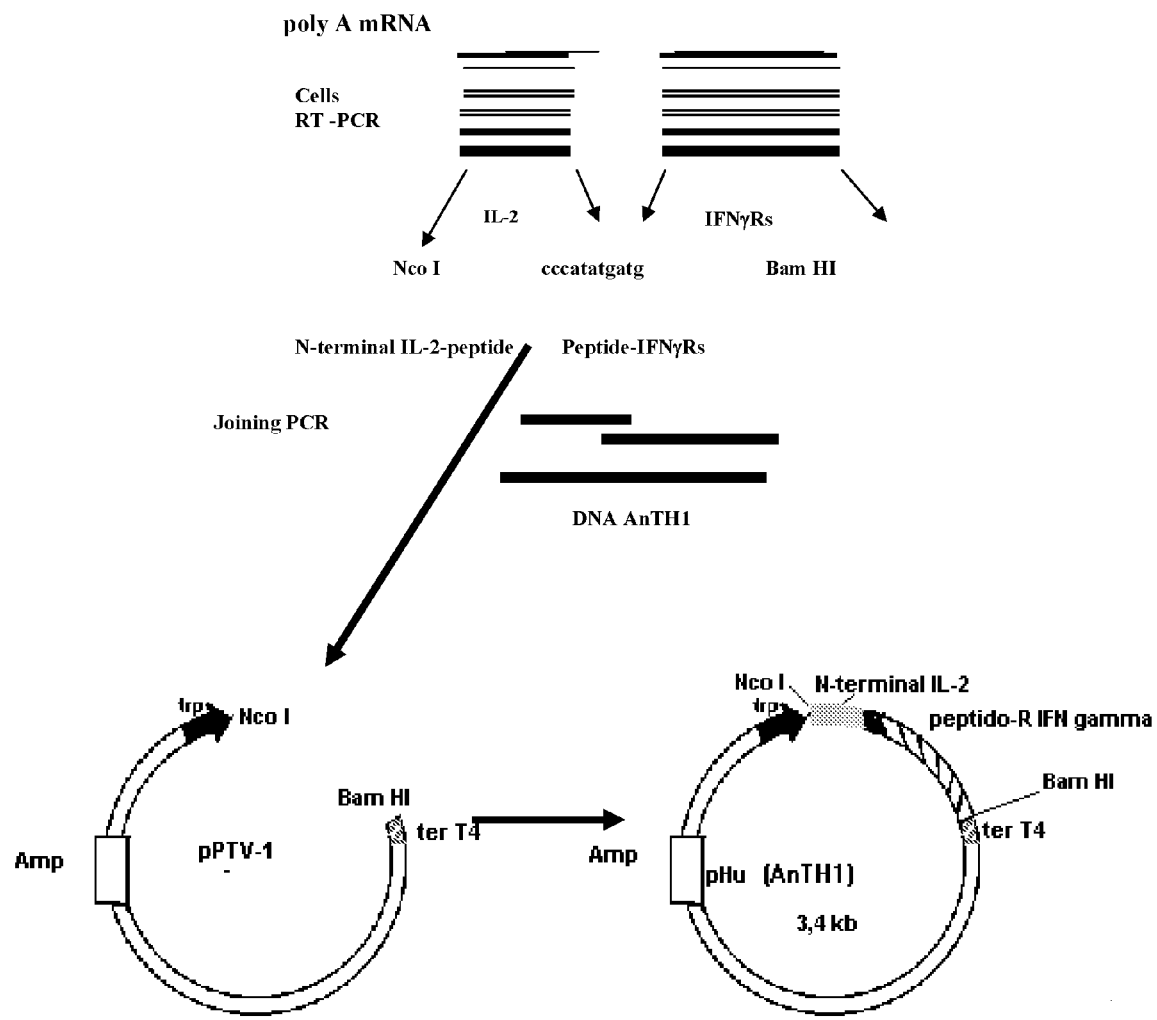

2 Claims, 10 Drawing Sheets a  b

Figure 10.

SAPTSSSTKKT$_{11}$QLQLEHLLLDLQMILNGINNYK$_{33}$NPKLTRM$_{40}$LTFK$_{44}$F$_{45}$YMPK K$_{50}$ATELKH$_{56}$LQCLAHMMSR$_{66}$A$_{67}$EMGTADLGPSSVPTPTNVTIESYNMNPIVY WEYQ$_{101}$IMPQVPVFTVEVK$_{114}$NYGVKN$_{120}$SEWIDACINISHHYCNISDHVGDPSNS WVR$_{151}$VKARVGQKESAYAKS$_{166}$EEFAVCR$_{173}$DGKI$_{177}$GPPK$_{181}$LDIRKEEKQ$_{190}$IMIDIF HPSVFVNGDEQEVDYDPETTCYIR$_{220}$V$_{221}$YNVYVR$_{227}$M$_{228}$NGSEIQYK$_{236}$ILTQKEDD CDEIQCQLAIPVSSLNSQYCVSAEGVLHVWGVTTEKSKEVCITIFNSSIKG    (Seq. ID. No. 9)

CHIMERIC ANTAGONIST ANTH1

This application is a U.S. National Phase Application of International Application No. PCT/CU03/00006 filed on May 8, 2003. The specification of International Application No. PCT/CU03/00006 is hereby incorporated by reference in its entirety.

This application also asserts priority to Cuban Application No. CU2002/0095 filed on May 10, 2002. The specification of Cuban Application No. CU2002/0095 is hereby incorporated by reference in its entirety.

BACKGROUND OF THE INVENTION

The present invention is related to biological science, biotechnology and medical science, in particular with a drug that may inhibit the biological activities of interleukin-2, (IL-2) and gamma Interferon (IFN γ), two cytokines that act in the regulation of several functions of the body, that show increased amounts when found in a pathological state. This in turn avoids the inactivation of the immune system that endangers the lives of patients.

The production of cytokines by T helper lymphocytes (CD4+) and by cytotoxic T lymphocytes (CD8+) generate a pattern of cytokine production that have been identified as Th1 and Th2. The Th1 pattern is characterised by the production of IL-2, a tumor necrosis alpha (TNF α) and IFN γ, while Th2 pattern responds to the production of IL-4, IL-5, IL-6 and others. This type of response plays an important role in the body protection, as well as being the promoters of different immunopathological reactions.

There are a series of situations in which the inflammatory and uncontrolled immune reactions lead to the presence, development and perpetuation of inflammatory and autoimmune diseases. There are demonstrated examples on the pathological roles of the IL-2 and IFN γ in some of these diseases.

Multiple sclerosis is a degenerative demyelenating autoimmune disease. The role of IFNγ is very clear for this autoimmune disorder. Hence, it has been demonstrated in a clinical trial using IFNγ that this treatment produces the exarcebation of the disease (Panitch H S. et al. *Exacerbations of multiple sclerosis in patients treated with interferon gamma. Lancet* 1, 893-5, 1987.). It has also been demonstrated that the levels of messenger RNA, as well as the protein corresponding to IL-2 and IFNγ are found to be high in patients suffering from this disease (Lin J. et al. *IL-2, IFN-gamma, and TNF-alpha mRNA expression in peripheral blood mononuclear cells in patients with multiple sclerosis.* Chung Kuo I Hsueh Ko Hsueh Yuan Hsueh Page 19, 24-8, 1997). The production of these two cytokines by patient's cells has suggested their use as markers of the relapse of multiple sclerosis (Philippe J. et al. *In vitro TNF-alpha, IL-2 and IFN-gamma production as markers of relapses in multiple sclerosis. Clin Neurol Neurosurg* 98, 286-90, 1996). It has also been observed that the IL-2 and IFNγ are involved in the activation of non-specific lymphocytes that lead to the demyelination of the central nervous system (Martino G. et al. *Proinflammatory cytokines regulate antigen-independent T-cell activation by two separate calcium-signaling pathways in multiple sclerosis patients. Ann Neurol* 43, 340-49, 1998). A clinical trial is being carried out using an anti-IL-2 antibody known as Daclizumab in patients with this disease that do not respond to therapy with β IFN.

Lupus erythematosus is another systemic autoimmune disease where the presence of high levels of IL-2 and IFNγ have been associated to exacerbations of this disease (Viallard J F. et al. *Th1 (IL-2, interferon-gamma (IFN-gamma)) and Th2 (IL-10, I cytokine production by peripheral blood mononuclear cells (PBMC) from patients with systemic lupus erythematosus (SLE). Clin Exp Immunol* 115, 189-95, 1999). On the other hand, the absence of the receptor for IFNγ decreases the production of autoantibodies in lupus animal models (Haas C. et al. *IFN-gamma receptor deletion prevents autoantibody production and glomerulonephritis in lupus-prone (NZBxNZW)F1 mice. J Immunol* 160, 3713-18, 1998) and the presence of the soluble receptor for IFNγ inhibits the presence of the disease (Ozmen L. et al. *Experimental therapy of systemic lupus erythematosus: the treatment of NZB/W mice with mouse soluble interferon (receptor inhibits the onset of glomerunephritis. Eur J Immunol.* 25, 6-12, 1995). This was recently tested using a murine lupus model with a chimeric protein containing the extracellular region of the IFNγ fused to the Fc fraction of the immunoglobulins (Lawson B R. et al. *Treatment of murine lupus with cDNA encoding IFN-gammaR/Fc. J Clin Invest.* 106, 207-15, 2000). The efficacy, however of this type of molecule in lupus erythematosus could be limited by a demonstrated dysfunction of the Fc receptor in patients with lupus erythematosus (Frank M M. et al. *Defective reticuloendothelial system Fc-receptor function in systemic lupus erythematosus. N Engl J Med* 300, 518-23, 1979, Dijstelbloem H M. et al. *Fcgamma receptor polymorphisms in systemic lupus erythematosus: association with disease and in vivo clearance of immune complexes. Arthritis Rheum* 43, 2793-800, 2000).

Myasthenia gravis is considered an organ-specific autoimmune disease mediated by anti-acetyl coline receptor autoantibodies and dependent on T cells, characterized by muscular weakness and fatigue. It was recently demonstrated that the IFNγ favors the formation of autoantibodies against the acetyl coline receptor; while the absence of the IFNγ receptor decreases the susceptibility to the disease in animal models (Zhang G X. et al. *Mice with IFN-gamma receptor deficiency are less susceptible to experimental autoimmune myasthenia gravis. J Immunol* 162, 3775-81, 1999). The IL-2 and other cytokines contribute, together with the IFNγ to the development of the disease (Zhang G X. et al. *Cytokines and the pathogenesis of myasthenia gravis. Muscle Nerve.* 20, 543-51, 1997).

In type 1 Diabetes (insulin dependent) or Diabetes mellitus, the beta cells of the pancreas are destroyed by an autoimmune mechanism. There is in vitro evidence that the IFNγ may be toxic for the beta cells of the pancreas (Sternesjo J. et al. *Effects of prolonged exposure in vitro to interferon gamma and tumor necrosis factor-alpha on nitric oxide and insulin production of rat pancreatic islets. Autoimmunity* 20, 185-90, 1995, Dunger A. et al. *Tumor necrosis factor-alpha and inter-feron-gamma inhibit insulin secretion and cause DNA damage in unweaned-rat islets. Extent of nitric oxide involvement. Diabetes* 45, 183-9, 1996, Baldeon M E. et al. *Interferon-gamma independently activates the MHC class I antigen processing pathway and diminishes glucose responsiveness in pancreatic beta-cell lines. Diabetes* 46, 770-8, 1997). However, other studies demonstrate that the action of the IFNγ on the cells producing insuline in the pancrease is indirect (Sarventick N. et al, *Loss of pancreatic islet tolerance induced by beta-cell expression of interferon-gamma. Nature,* 346, 844-7, 1990). Most probably, its action is activated through macrophages for the production of IL-1, TNFα and nitric oxide that do act directly on the beta cells and stimulate the expression of MHC I in beta cells, thus favoring their destruction by cytotoxic lymphocytes (Thomas H E. et al. *IFN-gamma action on pancreatic beta cells causes class I MHC upregulation but not diabetes. J Clin Invest,* 102, 1249-57, 1998, Thomas H E et al. *Beta cell destruction in the* development of autoimmune diabetes in the non-obese diabetic (NOD) mouse. *Diabetes Metab Res Rev* 16, 251-61, 2000). It has also been shown that the absence of the IFNγ delays the appearance of diabetes, although it does not prevent it (Hultgren B. et al. *Genetic absence of gamma-interferon delays but does not prevent diabetes in NOD mice. Diabetes* 45, 812-7, 1996). Several reports show how the inactivation of the biological activity of IFNγ may be used to prevent diabetes (Debray-Scahs M. et al. *Prevention of diabetes in NOD mice treated with antibody to murine IFN gamma. J Autoimmun* 4, 237-48, 1991, Moosmayer D. et al. *A bivalent immunoadhesin of the human interferon-gamma receptor is an effective inhibitor of IFN-gamma activity. J Interferon Cytokine Res* 15, 1111-5, 1995, Prud'homme G J. et al. *Prevention of autoimmune diabetes by intramuscular gene therapy with a nonviral vector encoding an interferon-gamma receptor/IgG1 fusion protein. Gene Ther* 6, 771-7, 1999). It has also been seen that IL-2 as an activator of T lymphocytes can contribute to this reaction in the destruction of cells producing insulin. A clinical trial was recently started for the treatment of type 1 diabetes in children/adolescents of between 10 and 21 years of age with a recent diagnosis of the disease using the antibody anti IL-2 Daclizumab (Riley Hospital for Children. Project: Prevention of Diabetes Progression Trial (PDPT). www.rileyhospital.org.). This study has been designed to prevent the progression of the destruction of beta cells in recently diagnosed children.

The rejection to grafts is a complex process in which the cell mediated immunity and the circulating antibodies play an important role. The standard anti-rejection therapies use combinations of drugs such as cyclosporin, rapamycin, azatioprin, steroids and others. However, even with this therapy, more than 50% of the persons receiving the kidneys slowly reject their graft in 10 years. The graft disease against the host is the main cause of death among patients grafted with bone marrow. In these reactions that prevent grafts and compromises the lives of the grafted patients it has been demonstrated that both the IL-2 and the IFNγ contribute to their development (Hu H Z. et al. *Kinetics of interferon-gamma secretion and its regulatory factors in the early phase of acute graft-versus-host disease. Immunology* 98, 379-85, 1999, Nakamura H. et al. *Serum levels of soluble IL-2 receptor, IL-12, IL-18, and IFN-gamma in patients with acute graft-versus-host disease after allogeneic bone marrow transplantation. J Allergy Clin Immunol.* 106, S45-50. 2000).

Reumatoide arthritis (RA) is a chronic systemic disorder of unknown ethiology, characterized by inflammation, sinovial hyperplasia and the destruction of the affected joints. IL-2 is generally considered a pro-inflammatory citokine that exacerbates the state of type Th1 diseases such as autoimmune arthritis. Recent studies have shown that the IL-2 messenger RNA is increasing during the acute phase of the arthritis induced by a collagen in an animal model (Thornton S. et al. *Heterogeneous effects of IL-2 on collagen-induced arthritis. J Immunol* 165, 1557-63, 2000). On the other hand, the exacerbation of the disease has been found in animal models to be associated to IFNγ increase (Tellander A C. et al. *Potent adjuvant effect by anti-CD40 in collagen-induced arthritis. Enhanced disease is accompanied by increased production of collagen type-II reactive IgG2a and IFN-gamma. J Autoimmun* 14, 295-302, 2000). Both the IL-2 and the IFNγ have been significantly increased in the sinovial tissue of patients with RA (Canete J D et al. *Differential Th1/Th2 cytokine patterns in chronic arthritis: interferon gamma is highly expressed in synovium of rheumatoid arthritis compared with seronegative spondyloarthropathies. Ann Rheum Dis* 59, 263-8, 2000).

The inflammatory disease of the intestine consists of two gastrointestinal disorders: Crohn disease and ulcerative colitis. These diseases are characterized by the chronic inflammation of the intestine. Crohn disease is an inflammatory disorder that is extended around the internal line of the intestinal wall and penetrates in its deepest layers. This inflammation can be found in any part of the digestive system (esophagus, stomach, small intestine, large intestine or the anus). The Protein Desig Labs company has announced the start of phase I/II clinical trials in patients with moderate to severe crohn disease using an anti IFNγ antibody (SMART Anti-Gamma Interferon Antibody) (Fremont, Calif. *Protein Design Labs Announces Phase I/II Trial of SMART" Anti-Gamma Interferon Antibody in Crohn's Disease*. Protein Design Labs, Inc. (Nasdaq), Jan. 10, 2001). Ulcerative colitis is confined to the mucose and sub-mucose of the large intestine (the colon or rectus). Recently, in the Annual Congress of the American Association of Gastroenterology it was shown how the decrease in the levels of IFNγ in the bloodstream is a remission marker in a mouse model for colitis (Yaron I. *Annual meeting of the American Gastroenterology Association*. May 20-23, 2001. Georgia World Congress Center. Atlanta, Ga.).

Septic shock is the result of the dissemination of microorganisms of revere infections through the bloodstream. This is more frequently produced by Gram-negative bacilli acquired at the hospitals and it is more common in immunocompromised patients and those having chronic diseases. In ⅓ of the patients it is produced by Gram-positive germs and by *Candida albicans*. Both in the septic shock produced by the gram negative and the Gram positive bacteria, the IFNγ and the IL-2 contribute to the lethality of the inflammatory reactions in which they participate. The IFNγ is a lethal mediator in animal models with septic shock (Heremans H. et al. *Interferon gamma, a mediator of lethal lipopolysaccharide-induced Shwartzman-like shock reactions in mice. J Exp Med* 171, 1853-69, 1990, Wysocka M. et al. *Interleukin-12 is required for interferon-gamma production and lethality in lipopolysaccharide-induced shock in mice. Eur J Immunol* 25, 672-6, 1995, Kuschnaroff L M et al. *Increased mortality and impaired clonal deletion after staphylococcal enterotoxin B injection in old mice: relation to cytokines and nitric oxide production. Scand J Immunol* 469-78, 1997). As is the case for animal models of other diseases, the absence of IFNγ receptor in these animals make them resistant to endotoxic shock (Car B D et al. *Interferon gamma receptor deficient mice are resistant to endotoxic shock. Exp Med* 179, 1437-44, 1994). Similarly, several reports show the participation of IL-2 in the development and lethality of septic shock (Micusan V V, et al. *Production of human and murine interleukin-2 by toxic shock syndrome toxin-1. Immunology* 58, 203-8, 1986, Arad G, et al. *Superantigen antagonist protects against lethal shock and defines a new domain for T-cell activation. Nat Med.* 6, 378-9, 2000, Stevens D L. et al. *Streptococcal toxic shock syndrome associated with necrotizing fasciitis. Annu Rev Med* 51, 271-88, 2000). Mononuclear cells grown in vitro with IL-2 segregate secondary cytokines such as IL-1, TNFα and IFNγ are implicated in the pathophysiology of septic shock.

Vulgar psoriasis is a complex and multigenic skin disease that is potentially mediated by pro-inflammatory cytokines produced by damaged T cells. An unappropriate chronic expression of these cytokines leads to the immune activation of cells and to tissue damage. This is characterised by an excessive production of skin cells and the generation of blood vessels that are probably responsible for the redness and plate formation that are part of this disease. The pathological role of IFNγ and IL-2 has been evidenced for psoriasis. Most of the epidermal cells in vulgar psoriasis produce IL-2, IFNγ and TNFα that are defined as T cytotoxic cells. High levels of IFNγ and IL-2 and not of IL-4 have been detected in psoriasis patients. This may be related to disbalance in T cell populations that contribute to a sustained or chronic immune activation of these cells (Schaak J F et al. *T cells involved in psoriasis vulgaris belong to the Th1 subset. J Invest Dermatol* 102, 145-9, 1994, Austin L M, et al. *The majority of epidermal T cells in Psoriasis vulgaris lesions can produce type 1 cytokines, interferon-gamma, interleukin-2, and tumor necrosis factor-alpha, defining Tc1 (cytotoxic T lymphocyte) and TH1 effector populations: a type 1 differentiation bias is also measured in circulating blood T cells in psoriatic patients. J Invest Dermatol* 113, 752-9, 1999). An encouraging result using Daclizumab has been showing for psoriasis treatment (Krueger J M et al. *Successful in vivo blockade of CD25 (hihg-affinity interleukin 2 receptor) on T cells by administration of humanized anti-Tac antibody to patients with psoriasis. J Am. Acad. Dermatol.* 43, 448-58, 2000). Recently a new trial has been started with this drug (Fremont, Calif. *Protein Design Labs Presents Three Humanized Antibodies in Clinical Development for Psoriasis at International Psoriasis Symposium.* Jun. 22, 2000. Protein Design Labs, Inc. (PDL) Nasdaq).

There are other less studied diseases where the use of an antagonist against the IL-2 and the IFNγ can also be of use; in this case there is atherosclerosis and ischemia/reperfusion. Atherosclerosis and post-grafting atherosclerosis are characterized by the expansion of the arterial intima as a result of the infiltration of mononuclear leukocytes, the proliferation of vascular smooth muscle cells and the accumulation of extracellular matrix, as well as the presence of IFNγ (Ross R. *Atherosclerosis—an inflamatory disease. N. Engl. J. Med.* 340, 115-26, 1999, Hansson G K et al. Immune mechanisms in atherosclerosis. Arteriosclerosis 9, 567-78, 1989, y Libby P et al. *Functions of vascular wall cells related to development of transplantation-associated coronary arteriosclerosis. Transplant. Proc.* 21, 3677-84, 1989). It has been demonstrated that the exogenous IFNγ increases the atherosclerosis in an animal model (Whitman S C et al. *Exogenous interferon-gamma enhances atherosclerosis in apolypoprotein E-/- mice. Am J Pathol* 157, 1819-24, 2000). On the other hand, it has been demonstrated that the neutralization of IFNγ in the serum, as well as the absence of its gene, decreases the extension of the expansion of the intima (Gupta S et al. *IFN γ potentiates atherosclerosis in ApoE knock-out mice. J. Clin. Invest.* 99, 2752-61, 1997, Nagano H et al. *Interferon γ deficiency prevents coronary arteriosclerosis but not myocardial rejection in transplanted mouse hearts. J. Clin. Invest.* 100, 550-57, 1997, Räisänen-Sokolowski, A. et al. *Reduced transplant arteriosclerosis in murine cardiac allografts placed in interferon γ knockout recipients. Am. J. Pathol.* 152, 359-65, 1998). More recently it was proven that the IFNγ promoted atherosclerosis action in the absence of leukocytes (Tellides G et al. *Interferon γ elicits arteriosclerosis in the absence of leukocytes. Nature* 403, 207-11, 2000). Ischemia and reperfusion are characterized by the interruption of blood flow in an area, with the consequent elimination of oxygen and nutrient supply and the reperfusion and total or partial restoration of blood flow to the tissue that was ischemic, which is clinically frequent. It can be observed during hypovolemic and septic shock, myocardium infarct, embolism, compartimental syndrome, freezing, organ graft, etc. Tissue hypoxia, in any case, produces an alteration of the cell metabolism from which constantly better-known complex biochemical and molecular modifications are derived. The damage due to repperfusion consequently produces cellular death and endothe-lial dysfunction produced by the restoration of blood tissue. IFNγ and IL-2 have been reported to be mediators of the damage produced on the organs through ischemia and reperfusion (Serrick C et al. *The early release of interleukin-2, tumor necrosis factor-alpha and interferon-gamma after ischemia reperfusion injury in the lung allograft. Transplantation* 58, 1158-62, 1994, Marck A R C et al. *Ischemia/Reperfusion-Induced IFN-gamma Up-Regulation: Involvement of IL-12 and IL-18. The Journal of Immunology* 162, 5506-10, 1999). Several authors have described antagonists against IFNγ. The inhibition of the antiviral activity of the human IFNγ humano by its recombinant soluble receptor has been described in the European patent EP 0 393 502 A1. It has also been described that the recombinant soluble receptor for murine IFNγ inhibits the presence of glomerulonephritis in mice (Ozmen L. et al. *Experimental therapy of systemic lupus erythematosus: the treatment of NZB/W mice with mouse soluble interferon-gamma receptor inhibits the onset of glomerulonephritis. Eur J Immunol.* 25, 6-12, 1995). Three murine IFNγ have been constructed. These consist of chimeric proteins formed by the extracellular region of the receptor in mice for IFNγ and constant domains of immunoguline molecules. These constructions neutralize the antiviral activity of the mouse IFNγ and have a prolonged mean life in the blood (Cornelia K. et al. *Construction, purification, and characterization of new interferon gamma (IFN γ) inhibitor protein. J. Biol. Chemistry.* 267, 9354-60, 1992 and European patent EP 0 614 981 A1). The potential use of a fragment of immunoglobulin or its Fc region fused to the soluble IFNγ receptor to be used in lupus erythematosus in humans can be limited by a demonstrated dysfunction of the receptor for the Fc of this autoimmune dysorder (Frank M M et al. *Defective reticuloendothelial system Fc-receptor function in systemic lupus erythematosus. N Engl J Med.* 300, 518-23, 1979). This type of inhibitor is monofunctional and it therefore has a smaller scope of action.

In mice, the use of neutralizing anti-IFNγ antibodies decreases the expressions of the graft disease against the host (Mowat A. et al. *Antibodies to IFN gamma prevent immunologically mediated intestinal damage in murine graft-versus-host reaction. Immunology* 68, 18-23, 1989). In a skin allograft study, anti-IFNγ antibodies inhibited the rejection only if the graft was incompatible with the MHC class II antigens. This would suggest that the IFNγ constributes to the rejection of the allograft through the induction of MHC class II antigens (Rosenberg A. et al. *Specific prolongation of MHC class II disparate skin allografts by in vivo administration of anti-IFN gamma monoclonal antibody. J. Immunol.* 144, 4648-50, 1990). Single strand antibodies with a variable region (scFv) against human IFNγ expressed in bacteria have also been obtained and proven to be efficient in neutralizing the biological activity of murine IFNγ (Froyen G. et al. *Bacterial expression of a single-strand antibody fragment (scFv) that neutralizes the biological activity of human interferon γ. Mol Immunol.* 30, 805-12, 1993). The use of antibodies in human therapy faces the problem of the responses of the host against the immunogenic regions of these heterologous molecules, and in the cases of chimera and humanized antibodies, to the loss of affinity and specificity (Merluzzi S et al. *Humanized antibodies as potential drugs for therapeutic use. Adv Clin Path,* 4, 77-85, 2000) as well as to expressions of toxicity (Clark M et al. *Antibodies to IFN gamma prevent immunologically mediated intestinal damage in murine graft-versus-host reaction. Immunology* 68, 18-23, 2000).

Other analogous solutions have also been described. Mixtures of a cytokine with its soluble receptor have been proposed, but its purpose was to potentiate the effect of the cytokines. In this case the cytokine and its receptor are independently produced and later mixed in one preparation as demonstrated in the American patent WO 94/21282. Cyclosporin A, FK506 and rapamycin are potent suppresors of the immune system, especially of T cells, that are used to prevent graft rejection. The first two, inhibit the signal transduction started by the antigen receptor to T cells that lead to the transcription of the early activation genes. This includes the transcription of the gene that codifies for the IL-2 needed for the transition of the state of rest G0 to phase G1 of the cell cycle. Rapamycin has no effect of the early synthesis of the cytokines by the T cells, but it inhibits the response of these cells to the IL-2 required for the transition from phase G1 to S of the cell cycle (Waldmann T. A. et al. *The IL-2/IL-2 receptor system: a target for rational immune intervention. Immunology Today* 14, 264-70, 1993). Rapamycin allows the specific activation of T cells but avoids their clonal expansion through the interference with signaling by means of the beta strand of the IL-2 receptor (RβIL-2) (Woerly G. et al. *Effect of rapamycin on the expression of the IL-2 receptor (CD25). Clin Exp Immunol* 103, 322-7, 1996). Cyclosporin A, has significantly increased the survival of renal allografts, while it also decreases autoimmune diseases. The use of these immunosuppressors has been limited, because of their toxic effects that include gastrointestinal complications, gum hypertrophia and especially dose dependent nephrotoxicity, and hypertension. (Hortelano S. et al. *Potentiation by nitric oxide of cyclosporin A and FK506-induced apoptosis in renal proximal tubule cells. J Am Soc Nephrol* 11, 2315-23, 2000, Tsimaratos M et al. *Kidney function in cyclosporine-treated paediatric pulmonary transplant recipients. Transplantation* 69, 2055-9, 2000). Monoclonal antibodies that block the interaction of IL-2 with its receptor have been used in animal models to inhibit the graft-versus-host disease and the rejection of allografts. These antibodies were also used in rodents to suppress autoimmune disorders. In clinical trials, the antibodies against the alpha strand of the IL-2 receptor (RαIL-2) improved the graft disease against the host that was resistent to steroid treatment. However, these efforts are limited because of the antigenicity of these antibodies. Single strand antibodies of variable region have been found to inhibit the union of the IL-2 to the γ subunit of the IL-2 receptor and interfere with the biological activity of the IL-2 tested in the murine cell line CTLL-2 as described in the European patent EP 0 621 338 A2. The creation of humanized antibodies that improve this type of therapy, still have the drawbacks referred to previously. In this type of therapy monolonal antibodies conjugated with toxins or radioactively marked, have also been tested (Waldmann T. A. *Genetically engineered monoclonal antibodies armed with radionuclides. Year Immunol.* 7, 205-12, 1993). The use of toxins fused to antibodies anti IL-2 or IL-2 to eliminate cells that express the receptor for IL-2 and contribute to the development of pathogenical stages have been described as stated in the American patent WO 92/20701 and in the European patent EP 0 369 316 A2. The non-specific toxicity of the immunotoxins (Frankel A. E. et al. *Clinical trials of target toxins. Cancer Biology* 6, 307-17, 1995) as well as their immunogenicity (Chen S-Y. et al. *Design of genetic immunotoxin to eliminate toxin immunogenicity. Gene Therapy* 2, 116-23, 1995) has made the use of these drugs hardly recommendable. Anti IL-2 antibodies are being developed for the treatment of RA (Simon L S. et al. *New and future drug therapies for rheumatoid arthritis. Rheumatology (Oxford)* 39 *Suppl* 1:36-42, 2000). Antibodies targeted against the RαIL-2 are being used to avoid the rejection of kidney grafts (Olyaei A J et al. *Use of basiliximab and daclizumab in kidney transplantation. Prog Transplant* 11, 33-7, 2001). The limits of the use of antibodies in prolonged therapies have been described above.

The neutralization of pro-inflammatory cytokines such as TNFα (Beutler B. et al. *Passive immunization against cachectin/tumor necrosis factor protects mice from lethal effect of endotoxin. Science* 229, 869-71, 1989) or IL-1 (Natanson C. et al. *Selected treatment strategies for septic shock based on proposed mechanism of pathogenesis. Ann. Intern. Med.* 120, 771-83, 1994) decrease mortality due to sepsis in several animal models. However, in clinical trials using antagonists against IL-1 (antagonist of the IL-1 receptor) (Fischer C. J. et al. *Recombinant human interleukin-1 receptor antagonist in the treatment of patients with sepsis syndrome: results from randomized, double-blind, placebo-controlled trial. JAMA* 271, 1836-43, 1994) and against the TNFα (a recombinant chimeric protein: soluble receptor TNF/Fc) (Fischer C. J. et al. *Treatment of septic shock with tumor necrosis factor receptor.Fc fusion protein. N. Engl J. Med.* 334, 1697-1702, 1996) have not only not produced improvements but have also increased mortality due to the disactivation of the immune system. FDA has approved two antagonists against TNFα (Lipsky P E. et al. *Infliximab and Methotrexate in the Treatment of Rheumatoid Arthritis. N Engl J Med*, 343, 1594-1602, 2000) that have demonstrated favorable effects in the treatment of RA. One of these is an antibody against a subunit of the receptor for TNFα (Infliximab). The neutralization of the TNFα beyond certain levels may bring about a disactivation of the immune system as has been demonstrated in a model with rats having RA (Colagiovanni D B. et al. *TNF-alpha blockade by a dimeric TNF type I receptor molecule selectively inhibits adaptive immune responses. Immunopharmacol Immunotoxicol* 22, 627-51, 2000). A higher frequency of infections has been observed in patients treated with Infliximab than the control groups without it (placebo groups) (Schaible T F. *Long term safety of infliximab. Can J Gastroenterol* 14 *Suppl* C:29C-32C, 2000), as well as the appearance of auto-antibodies and the development of lupus (Markham A. et al. *Infliximab: a review of its use in the management of rheumatoid arthritis. Drugs* 59,1341-59, 2000). Etanercept is a chimeric protein that is bound to the soluble receptor for TNFα and the Fc portion of the IgG1 (Moreland L W et al, *Etanercept therapy in rheumatoid arthritis. A randomized, controlled trial. Ann Intern Med* 130, 478-86, 1999). Suspending the treatment produces a relapse of the patient; therefore, this drug does not cure the disease. This implies that the patient should be treated for long periods. Although in short term studies there have been no important adverse effects, a prolonged therapy might generate the presence of antibodies against the molecule (Russell E. et al. *Patients receiving etanercept may develop antibodies that interfere with monoclonal antibody laboratory assays. Arthritis Rheum* 43, 944-47, 2000). Several cases of patients treated with Etanercept have been reported to have developed fatal aplastic anemia, as well as pancytopenia, and demyelating syndromes (Klippel J H, *Biologic Therapy for Rheumatoid Arthritis. N. Engl J. Med.,* 343, 1640-1, 2000).

Until now, no antagonist against IFNγ has been clinically used. The use of cytokine antagonists to prevent, decrease or eliminate inflammatory and autoimmune reactions harming the body due to their temporal alteration or their chronicity, have been explored for many cytokines. Many of them have been uneffective. In some cases the antagonist is limited to a cytokine molecule and its scope of action and potency are limited, since the doses cannot be increased because of their toxicity. In those that have been able to neutralize the cytokine, this effect has been extreme and has produced a disactivation of important functions for the body (immune system).

The IL-2 interacts with its RαIL-2. This subunit is able to internalize the IL-2, which has been demonstrated for T and B lymphocytes and is probably recycled to the surface, while the other chains of this receptor are degraded after they are internalized (Hemar A. et al. *Endocytosis of interleukin 2 receptors in human T lymphocytes: distinct intracellular localization and fate of the receptor alpha, beta, and gamma chains. J Cell Biol* 129, 55-64, 1995). The IFNγ is internalized and degraded, while its receptor is recycled (Celada A. et al. *Internalization and degradation of receptor-bound interferon-gamma by murine macrophages. Demonstration of receptor recycling. J Immunol* 139, 147-53, 1987). The internalizing characteristics of the IL-2 by its IL-2R α, as well as that of the IFNγ by its receptor indicates a potential recycling, at least, of the extracellular region of the receptor for IFNγ forming part of the chimeric antagonist AnTh1. This will result in a prolongation of the presence of this molecule in the bloodstream, and therefore, of its effect.

The union or conjugation of two molecules frequently leads to a significant decrease or loss of the biological activity of the related molecules because of the conformational changes occurring or to the spatial interference produced as a result of the creation of a new molecule (Knusli, C et al. *Polyethylene glycol* (*PEG*) *modification of granulocyte-macrophage colony stimulating factor* (*GM-CSF*) *enhances neutrophil priming activity but not colony stimulating activity. Br J Haematol* 82, 654-63, 1992). Certain alternatives have been used, as for example in the U.S. Pat. No. 5,073,627 where there is a description of a union peptide that fuses the granulocyte colony-stimulating factor and macrophages (GM-CSF) with IL-3. A problem with this type of peptides is that they can be rigid and non-flexible. As a result of this the protein cannot move to adopt the precise conformation allowing it to carry out its biological activity properly. It is therefor also necessary to design and find peptides that may bind two molecules and at the same time allow each one of them to adopt the proper conformation, producing a biologically active molecule. Taking the latter into account safer, more effective and more specific immuno-suppressors and anti-inflammatory drugs are needed. It is therefore important to conceive a molecule with more functional versatility, that inhibits all the pathological activities or functions of the target drugs but that, at the same time, may allow the important functions for the body to take place, enabling its prolonged use without endangering the life of patients. An antagonist that may interfere with the simultaneous action of two cytokines and that may avoid immuno-paralization has not yet been designed.

DETAILED DESCRIPTION OF THE INVENTION

The essence of this invention is that of a recombinant chimeric protein called AnTH1 that is formed by a 60 amino acid fragment of the N-terminal region of the human IL-2 fused through a 4 amino acid peptide to the N-terminal extracellular region of the alpha subunit of the receptor for IFNγ containing 228 amino acids. This protein has a growth stimulating activity of T cells, it inhibits the growth stimulating activity of T cell induced by IL-2, it inhibits the induction of HLA-II bγ IFNγ and it inhibits the antiproliferative activity of IFNγ. The DNA sequence corresponding to the first 60 amino acids of the N-terminal of human IL-2 and the binding peptide (SEQUENCE #5) and the sequence of the binding peptide and the DNA coding for the 228 amino acids of the extracellular region of the RαIFNγ (SEQUENCE #7) were obtained by reverse transcription of the RNA poly A from Jurkat and Raji cells respectively and amplified with specific primers through PCR (see example 1, SEQUENCE #1 and SEQUENCE #2, SEQUENCE #3, SEQUENCE #4). The DNA sequence corresponding to the binding peptide (SEQUENCE #6) was designed for that purpose and added to the primers used to amplify the region of the soluble receptor for RαIFNγ.

The present invention also describes the vector used for production in *E. coli* of the recombinant protein AnTH1, called pHu (AnTH1), which was deposited in the Belgian Coordinated Collections of Microoganism (BCCM), with the access number LMBP 4535 on May 6, 2002. This vector was prepared using recombinant DNA technology (Sambrook et al. *Molecular Cloning—A laboratory Manual, 2nd ed. Cold Spring Harbor, N.Y.* 1989). The latter vector was modified and finally contains a marker of choice, the tryptophane promoter, and the sequence that codifies for the 60 amino acids of human IL-2, the binding peptide and the 228 amino acids of the extracellular region of the Rα IFN γ (SEQUENCE #8). The final construction of the vector obtained is called pHu (AnTH1), (see example 2, FIG. 1).

The present invention also describes the transformed *E. coli* strain with the pHu vector (AnTH1). The pHu vector (AnTH1) was used to transform the *E. coli* W3110P3 strain. The *E. coli* W3110P3 strain containing the pHu vector (AnTH1) was grown and induced for the expression of the recombinant chimeric protein AnTH1. The strain achieves a high degree of expression of the protein (see example 4). This protein may be expressed in other host cells (insect cells, mammal cells and plant cells using the proper vectors). The present invention also describes the production of a recombinant chimeric protein with an adequate degree of purity for the evaluation of its biological activity through a process by which a preparation with 80-90% purity of the biologically active protein is obtained. The cellular pellet obtained through strain culture after induction, was processed for the extraction of the recombinant protein. Successive washed pellet procedures were carried out using solubilizing agents (denaturalizing) that allow the extraction of the protein of interest with a minimum amount of contaminant proteins from *E. coli*. After obtaining an adequate degree of purity (80-90%) using these procedures, the preparation containing the AnTH 1 protein was refolded. This procedure consists of slowly eliminating the denaturalizing agents. The process is illustrated in example 5.

The invention describes the biological activity of the recombinant protein AnTH1. This protein has a T cell growth stimulating activity (example 7). It is able to interfere with the stimulation of the proliferation of the T cells produced by the human IL-2 in the mouse cell line CTLL-2 (example 8). It is able to inhibit the antiproliferative activity of the human IFNγ in the cell line Hep-2 (example 9) and it also inhibits the stimulation by IFNγ of the HLA-II expression in COLO 205 cell line (example 10). The human IL-2, in contrast to IFNγ, can also act on murine cells.

This recombinant protein may be used in the preparation of a useful pharmaceutical composition for diseases where both IL-2 and IFNγ have a pathological role. These diseases may be of autoimmune type, such as multiple sclerosis, sistemic lupus erythematosus, miastenia gravis, insulin dependent diabetes mellitus, active chronic hepatitis and fulminant hepatitis; of the autoimmune/inflammatory type, such as reumatoide arthritis and psoriasis, as well as in the rejection of organs, the graft-versus-host disease and in inflammatory diseases such as septic shock and also for atherosclerosis.

A new method is created with this invention, to prevent, interfere, and/or eliminate the actions of two cytokines that have pathogenic functions in different diseases. Hence, the targest are increased in a more specific form. The use of a chimeric protein that may neutralize or interfere with two cytokine signalizing systems dealing with the same pathological situations will allow to amplify the scope of ways for their interference, and therefore for their efficacy. On having a certain T cell growth stimulating activity, this would avoid an undesirable inactivation of the immune system, allowing a more prolonged use in patients and entities requiring it. Therefore, the drug would be safer and more efficient. The aim of the present invention is to create a hetero-bivalent antagonist that may interfere with the functions of the human IL-2 and the IFNγ, amplifying the therapeutic possibilities of the molecule and avoiding adverse reactions.

Microorganism Deposit:

The pHu (AnTH1) plasmid was deposited under the Treaty of Budapest for the Protection of Microorganisms in the Belgian Coordinated Collections of Microoganism (BCCM), with the access number LMBP 4535 on May 6, 2002.

DESCRIPTION OF THE FIGURES

FIG. 1. Genetic construction plasmid pHu (AnTH1) for the expression of the recombinant chimeric protein AnTH1.

FIG. 2. Expression on *E. coli* of the chimeric protein AnTH1. Electrophoresis in 12.5% polyacrylamide gel under reducing conditions. a: molecular weight standar; b, c, d: negative control strain 0, 8 and 18 hours of induction; e, f, g: strain under induction conditions 0, 8, 18 hours containing plasmid pHu (AnTH1).

FIG. 3. Presence of the recombinant chimeric protein AnTH1 in the different stages of the semipurification process. A: Electrophoresis in 12.5% polyacrylamide gel under reducing conditions. In line a: molecular weight standard, b: fermentation, c: Urea 8 M extraction, d: fractions of the mixed gel filtration chromatography, e: mixture of fractions after the dialysis. B: "Western blot" using and anti—AnTH1 antiserum deluted 1:1000 in 1% PBS/non-fat milk, released from the anti-*E. coli* strain W3110 P3 antibodies. B: In lines a, b, c, d the same samples were applied and in the same order referred to in the electrophoresis of Figure A (no molecular weight standard was applied).

FIG. 4. Identification of the chimeric protein AnTH1 using "western blot". Anti-IL-2 (A) and anti-AnTH1 (B) antisera were used for the identification. The dilution factor for both was 1:1000. The AnTH1 preparation refolded after dialysis was used (line a), in line b IL-2 was applied.

FIG. 5. Binding assay of the human IFNγ marked with $I^{125}$ to the chimeric protein AnTH1 using "dot blot". Approximately 1 ul of the eluted fractions from the gel filtration chromatography in nitrocellulose membrane were used. The strips were incubated with IFNγ marked with $I^{125}$ (35 μCi/μg) in the absence (line a) and in the presence (line b) of an excess of human IFNγ (100 times more).

FIG. 6. Stimulating activity of the growth of T cells from the recombinant chimeric protein AnTH1. Bar 1: 2.8 ng/ml of IL-2, bar 2: 1.5 μg/ml of AnTH1, bar 3: culture media.

FIG. 7. Inhibition by the recombinant chimeric protein AnTH1 of the growth stimulating activity of human IL-2 on the mouse cell line CTLL-2 (results expressed in international units of IL-2).

FIG. 8. Results of the inhibition of the antiproliferative activity of the human IFNγ by the recombinant chimeric protein AnTH1. Bar 1: 4 IU/ml of γ IFN (4 ng/ml), bar 2: 4 IU/ml of γ IFN+50 μg/ml AnTH1, bar 3: 50 μg/ml AnTH1.

FIG. 9. Inhibition of the IFNγ induced HLA II by the recombinant chimeric protein AnTH1. Bar 1: Basal level (IFNγ=0 IU/ml), bar 2: IFNγ 500 IU/ml (0.5 μg/ml), bar 3: IFNγ 500 IU/ml+1.5 μg/ml AnTH1.

FIG. 10. Amino acid sequence (SEQ ID NO: 9) of recombinant chimeric protein AnTH1. Peptides defined by mass spectrometry are indicated.

EXAMPLES

Example 1

Isolation of the Complementary DNA Strands that Codify for the First 60 Amino Acids of the Human IL-2 and the Extracellular Region of the α Subunit of the Soluble Receptor of Human IFNγ (Rα IFN γs).

For the isolation of the human complementary DNA, Raji (Burkitt lymphoma, ATCC:CCL-86) and Jurkat (human acute T cell leukemia, ATCC: TIB-152) cells were grown in the medium RPMI 1640 supplemented with 10% bovine fetal serum in a 5 L flask with gentle shaking at 37° C. in a 5% $CO_2$ atmosphere. The extraction of total RNA from Jurkat and Raji cells was made through the Chomczyski method (Chomczyski P. et al. *Single-step method of RNA isolation by acid guanidium thiocyanate-phenol-chloroform extraction. Anal. Biochem.* 162, 156-9, 1987). Then, the RNA-poly A was extracted using a commercial messanger RNA isolation system (Isolation System Life Technologies Messagemakerr cat. #10551-018). The complementary DNA coding for the first 60 amino acids of the human IL-2 and the 288 amino acids of the extracellular amino terminal portion of the human Rα IFN γs were isolated by reverse transcription and amplified by PCR of the poly A RNA from the Jurkat and Raji cells respectively. Approximately 1-2 μg of poly A RNA was processed using random hexameres.

The sequences of the oligonucleotides (primers) used to amplify the complementary strand of the DNA for the first 60 amino acids of the human IL-2 are described in SEQUENCE #1 (primer 1) and SEQUENCE #2 (reverse primer 1). The sequences of the primers used to amplify the complementary strand DNA for the 228 amino acids of the amino terminal portion of the human Rα IFN γs are described in SEQUENCE #3 (primer 2) and SEQUENCE # 4 (reverse primer 2).

The amplified DNA coding for the first 60 amino acids of the human IL-2 and the binding peptide (SEQUENCE #5) were digested with the restriction enzyme Nco I (underlined in the sequence of primer 1, SEQUENCE # 1). Then the extraction with phenol-chloroform was carried out to eliminate the enzyme and the buffer. It was precipitated and resuspended in the appropriate buffer and stored at −70° C. See sequence of the binding peptide (SEQUENCE #6).

The amplified DNA coding for the binding peptide and the 231 amino acids of the Rα IFNγ (SEQUENCE #7) was filled at the cohesive ends with Klenow polimerase and purified as previously described. Then it was digested with the restriction enzyme BamH I (underlined in the sequence of the reverse 2 primer), and purified as described above. See sequence of the binding peptide (SEQUENCE #6).

The amplified bands (SEQUENCES #5 and #7) were mixed in the calculated proportions and in the appropriate buffer to obtain the amplification of a new band containing the DNA sequence corresponding to the first 60 amino acids of the human IL-2 bound to the corresponding sequence for the 231 amino acids of the extracellular region of the human RαIFNγ and by the sequence corresponding to the binding peptide (SEQUENCE #6). The new band was amplified by PCR.

The amplified DNA (SEQUENCE #8) was purified as previously described. The purified DNA was digested with the restriction enzyme Bam HI and processed to eliminate the enzyme and the buffer, as described. Later, the DNA was again digested with the NcoI enzyme and purified as described.

Example 2

Genetic Construction for the Expression of the Recombinant Chimeric Protein AnTH1.

The expression vector contains the strong tryptophane promoter. The vector was digested with the BamH I enzyme. Then the extraction was carried out with phenol-chloroform to eliminate the enzyme and the buffer and it was precipitated and resuspended in an appropriate buffer. Afterwards, it was digested with the Nco I enzyme. The vector was finally separated in a gel as previously described. Hence the vector contains the promoter for the tryptophane, a free cohesive site Nco I, a free cohesive site BamH I, the terminator T4 and gene for the resistance to ampicillin. The DNA corresponding to SEQUENCE #8 was ligated to the vector using the ligase T4 enzyme. The E. coli cells were transformed with the genetic construction. The transformants containing the complementary DNA fragment for the first amino acids of the human IL-2 were identified, as well as the binding peptide and the 231 amino acids of the human Rα IFN γs in the same direction as the tryptophane promoter by carrying out restriction analysis with enzymes Nco I and Eco RI. The resulting plasmid was called pHu (AnTH1) (see FIG. 1).

Example 3

Sequencing.

The final genetic construction was sequenced. The sequencing was used in the protocol based on the procedure of Sanger (Sanger F et al. *DNA sequencing with chain-terminating inhibitors. Proc. Natl. Acad. Sci. USA* 74, 5463-67, 1977). It was proven that the construction has a part of the genes coding for the IL-2 (60 amino acids starting from the amino end group) under control, and later, the sequence of nucleotides coding for the union peptide (SEQUENCE #6) bound to the region that codifies for the 228 amino acids of the amino end of the Rα IFN γs. See SEQUENCE #8.

Example 4

Expression in *E. coli* of the Recombinant Chimeric Protein AnTH1.

Figure 2:
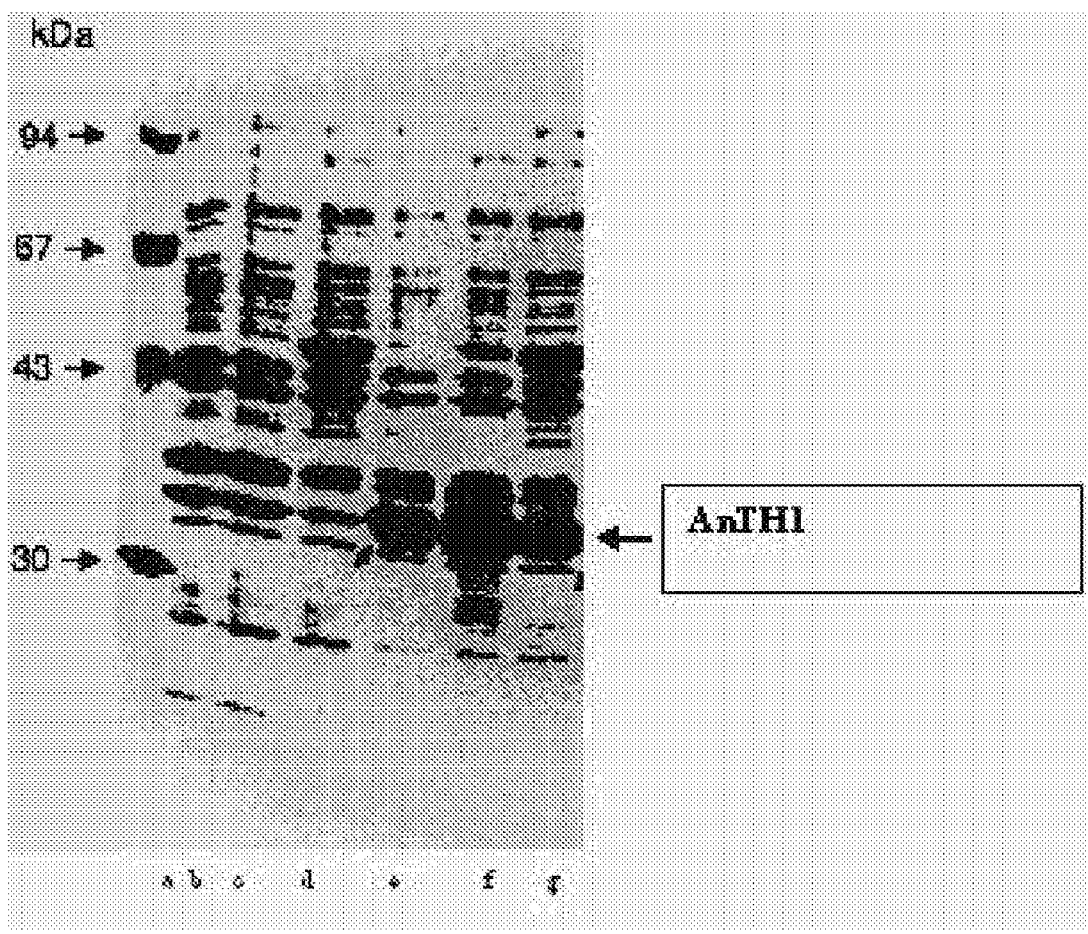

The host strain was *Escherichia coli* W3110 P3 (prototroph F-) and the plasmid pHu (AnTh1). For the expression, the plasmid was inoculated in 5 mL of the LB medium with ampicillin (50 µg/mL) and L-triptophan (100 µg/mL), and incubated at 37° C. for 6 hours while shaking. This culture was added to 50 mL of the LB medium and placed in a shaker at 100 r.p.m. for 6 hours at 37° C. This culture was added to 500 mL of the M9 medium (33 mM $Na_2HPO_4$, 2 mM $KH_2PO_4$, 8.5 mM NaCl, 18 mM $NH_4CL$, 0.1 mM $CaCl_2$, 1 mM $MgSO_4$), enriched with 0.2% hydrolized casein, 0.4% glucose, 50 µg/mL ampicillin, in such a way that the initial optic density of the culture (620 nm) was of 0.3. It is then incubated for 8 hours under the same conditions described above and finally, the cell sediment is collected through centrifugation (see FIG. 2).

Example 5

Extraction, Purification and Renaturalization of the Recombinant Chimeric Protein AnTH1.

Figure 3:
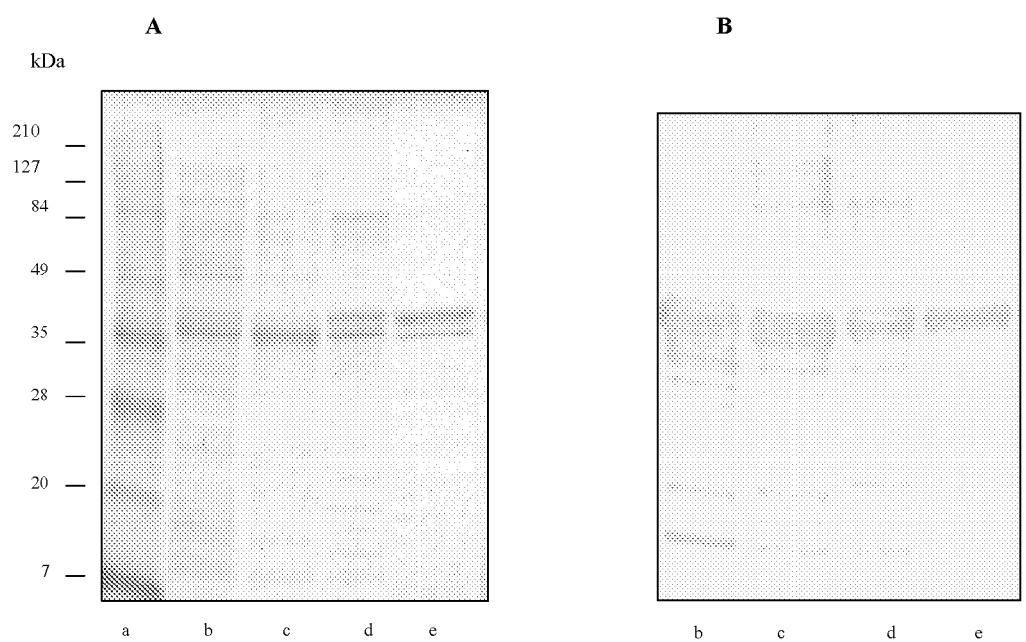
Figure 4:
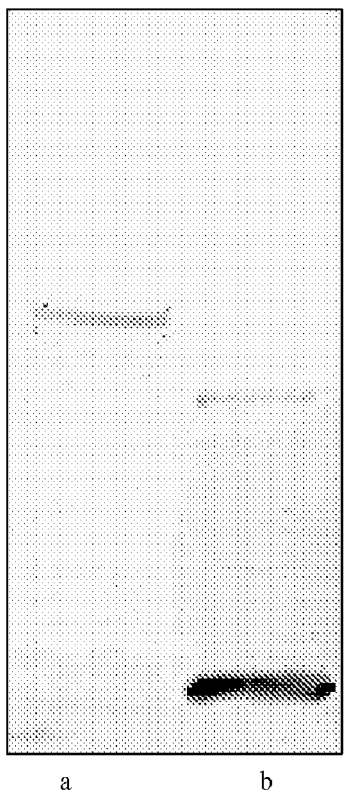
Figure 4:
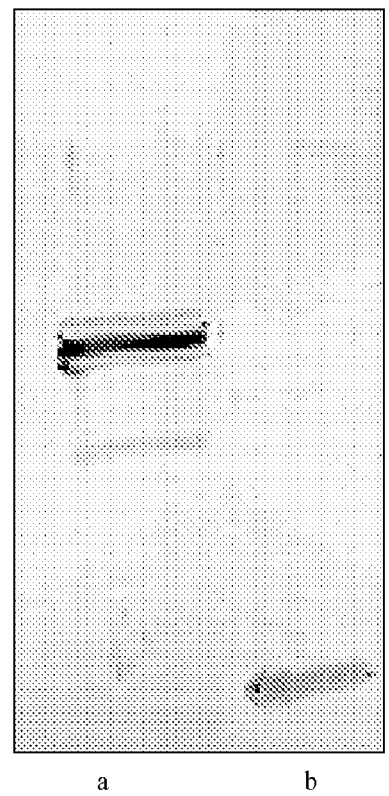

The cells are homogenized with polytron at a concentration of 0.1 g of the damp biomass per mL of the TE buffer (10 mM Tris HCl, 1 mM. EDTA pH 7.2). This suspension is submitted to an enzymatic rupture process with lysozime. The pellet obtained in the previous step is submitted to cell washing with different molarities of urea, from 1M to 8M, in 50 mM of Tris pH 7.2, 1 mM of EDTA. The homogenization is carried out with polytron. Initially it is homogenized for 1 minute, left to rest for 3 minutes and then again homogenized another minute. The whole process is carried out at 4° C. The proteins that are solubilized with urea, approximately 150 mL, were applied on a flow of 3 mL/minute on a K9/60 column (Pharmacia, Sweden), containing Sephadex G-100 resin that was previously equilibrated with 3 volumes of 50 mM of Tris HCL pH 9, 4M urea. The elution was carried out in the same buffer. The fractions containing the proteins were combined and dialyzed against 0.1 M of Tris HCl pH 9. Afterwards, the dialysis continued against the phosphate buffer saline (PBS) pH 7.4. (see FIG. 3 y 4)

Example 6

Binding of Gamma IFN to the Recombinant Chimeric Protein AnTh1.

Figure 5:
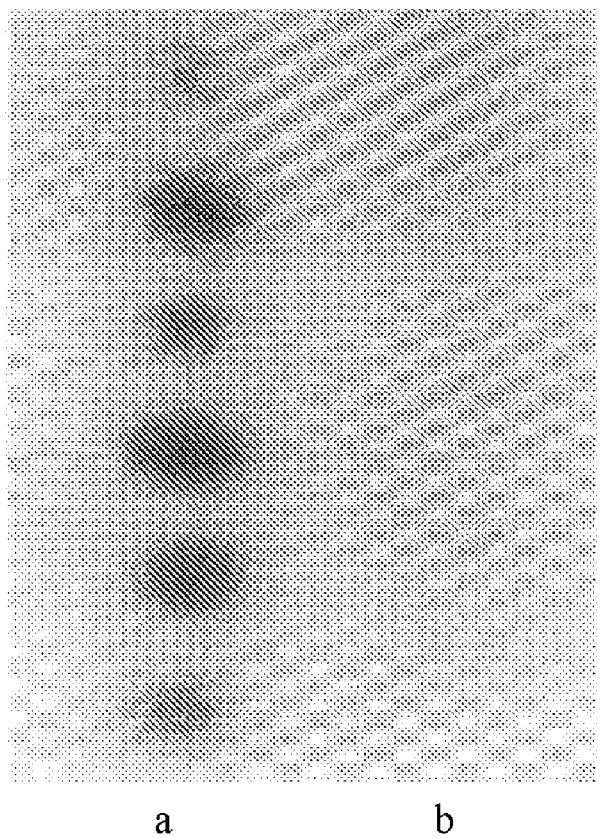

One microliter was applied (approximately 1 µg of total protein) of the recombinant chimeric protein AnTH1 after folding to nitrocellulose strips. The strips were incubated with 10% non-fat milk for 2 hours at room temperature (RT). The membranes were washed twice with Tris Buffer saline (TBS) for 5 minutes. After washing, the strips were incubated with gamma IFN marked with radioactive iodine ($^{125}$I-IFN gamma) 35 µci/µg for 1 hour at RT in the presence or absence of an excess of gamma IFN that was not marked. Afterwards, the nitrocellulose strips were washed twice with TBS for 5 minutes and then with TBS+0.03% Tween 20 for 5 minutes. Finally, radiographic films were exposed to the strips and stored at −70° C. for 72 h and then developed. (See FIG. 5).

Example 7

Stimulating Activity of the Growth of T Cells of the Recombinant Chimeric Protein AnTH1.

Figure 6:
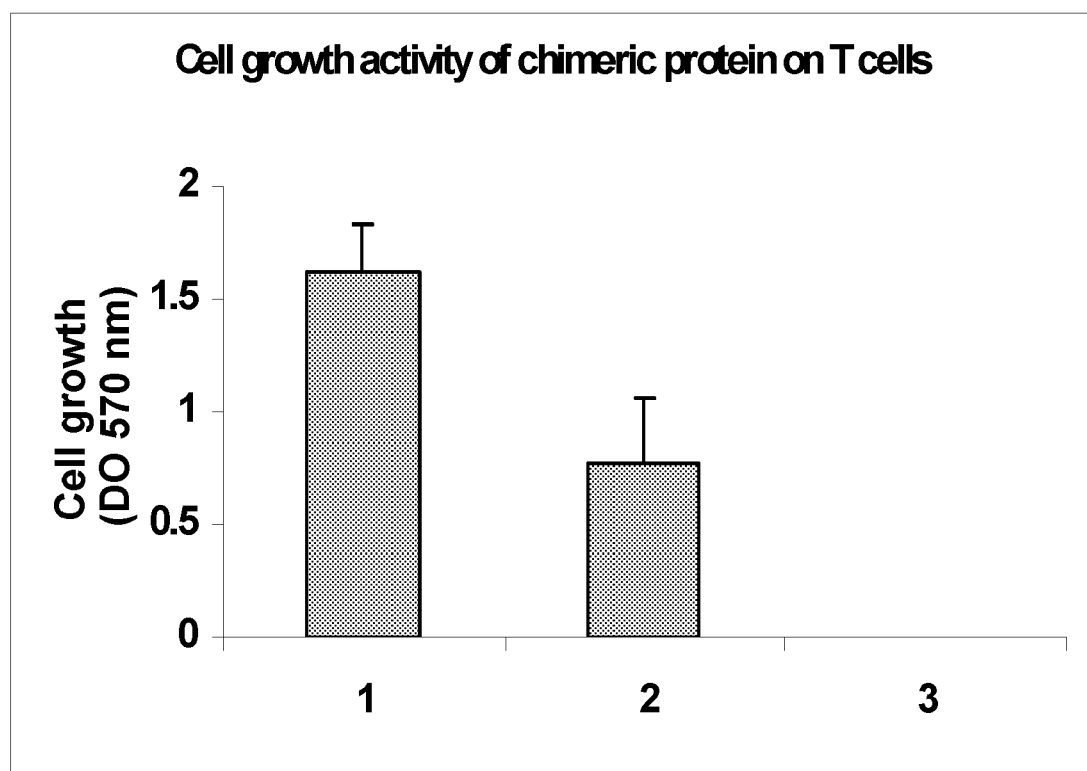

The biological activity of the recombinant chimeric protein AnTH1 was tested using the cell line of murine T lymphocytes dependent on IL-2. The cells were grown on the medium RPMI-1640 containing 1 mM pyruvate, 2 mM L-glutamine, 40 mM HEPES, 100 U/mL of penicillin, 50 µg/mL streptomycin, 50 µM 2-mercaptoethanol and 10% bovine fetal serum supplemented with 8 IU/mL of human recombinant interleukin-2 with a specific activity of $1.2 \times 10^7$ IU/mg. Before using the cells are washed 3 times, resuspended in the complete culture medium without IL-2 and incubated for 1 hour at 37° C. in a damp $CO_2$ atmosphere. Then the cells were washed, resuspended at a density of $4 \times 10^5$ cells/mL and distributed in plates of 96 wells (100 µl per well) containing 100 µl of serial dilutions 1:2 of rhIL-2 or samples (the recombinant chimeric protein AnTH1), in a complete medium. The international standard used in this trial was IL-2010397. After 36 hours of incubation at 37° C., 20 µl of 5 mg/mL of MTT ($C_{18}H_{16}N_5SBr$) were added to each well and the plates were incubated for 4 hours under the same conditions. Finally, 50 µl/pozo of the 10% SDS, 0.1 N HCl, 50% isopropanol were added, the plates were shaken for 1 hour at 37° C., and the absorbance was read at 570 nm using the plate reader. (See FIG. 6).

Example 8

Inhibition of the IL-2 Activity of Stimulating the Growth of T Cells with the Recombinant Chimeric Protein AnTH1.

Figure 7:
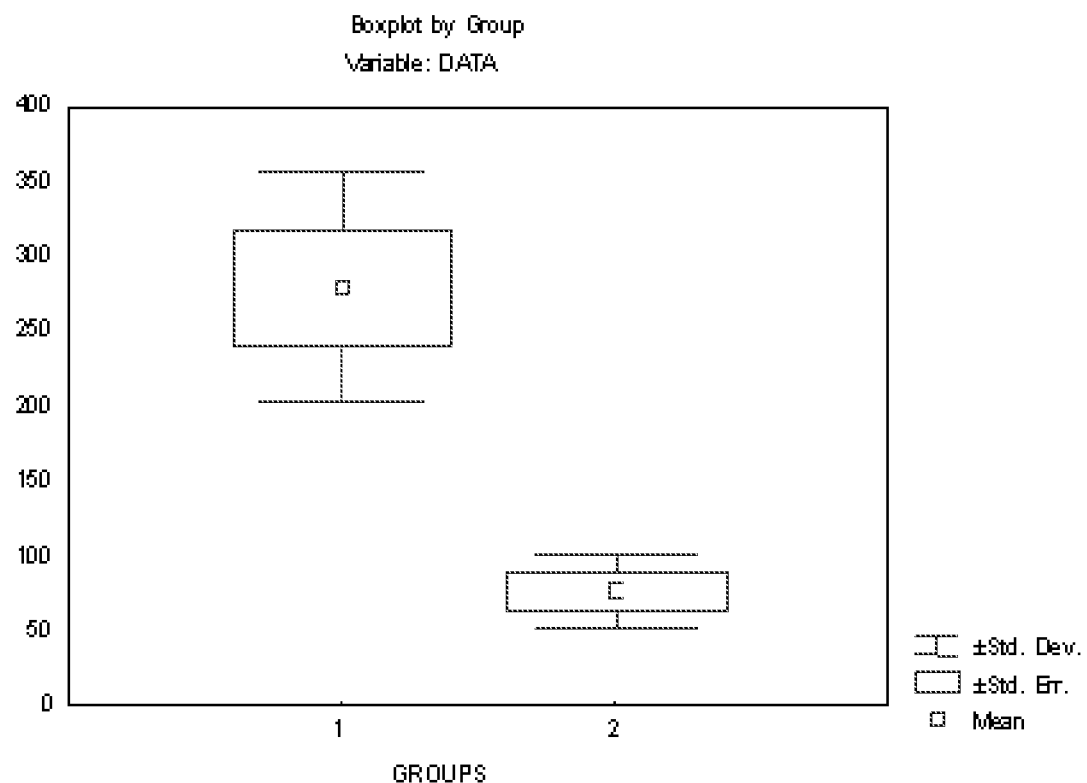

The biological activity for IL-2 was tested using the cell line of murine lymphocyte T dependent on IL-2. The cells were grown in a similar form as the previous experiment. Before they were used the cells were washed 3 times, resuspended in the complete culture medium without IL-2 and incubated for 1 hour at 37° C. in a humid $CO_2$ atmosphere. Then the cells were washed, resuspended at a density of $4\times10^5$ cells/mL and distributed in 96-well plates (100 µl per well) containing 100 µl of the serial dilutions 1:2 of rhIL-2 or samples (rhIL-2+the recombinant chimeric protein AnTH1 or the recombinant chimeric protein AnTH1 alone), in a complete medium. The international standard used in this trial was IL-2010397. After 36 hours of incubation at 37° C., 20 µl of 5 mg/mL of MTT ($C_{18}H_{16}N_5SBr$) were added to each well and the plates were incubated for 4 hours under the same conditions. Finally, 50 µl/well of the solution of 10% SDS, 0.1 N HCl, 50% isopropanol were added. Then the plates were shaken for 1 hour at 37° C., and the absorbance was read at 570 nm using a plate reader. The results were expressed as units of rhIL-2, based on the analyses of the data of the standard dilution curve of rhIL-2 and the serial dilutions of the sample (See FIG. 7).

Example 9

Inhibition of the Antiproliferative Activity of the γ IFN by the Recombinant Chimeric Protein AnTH1.

Figure 8:
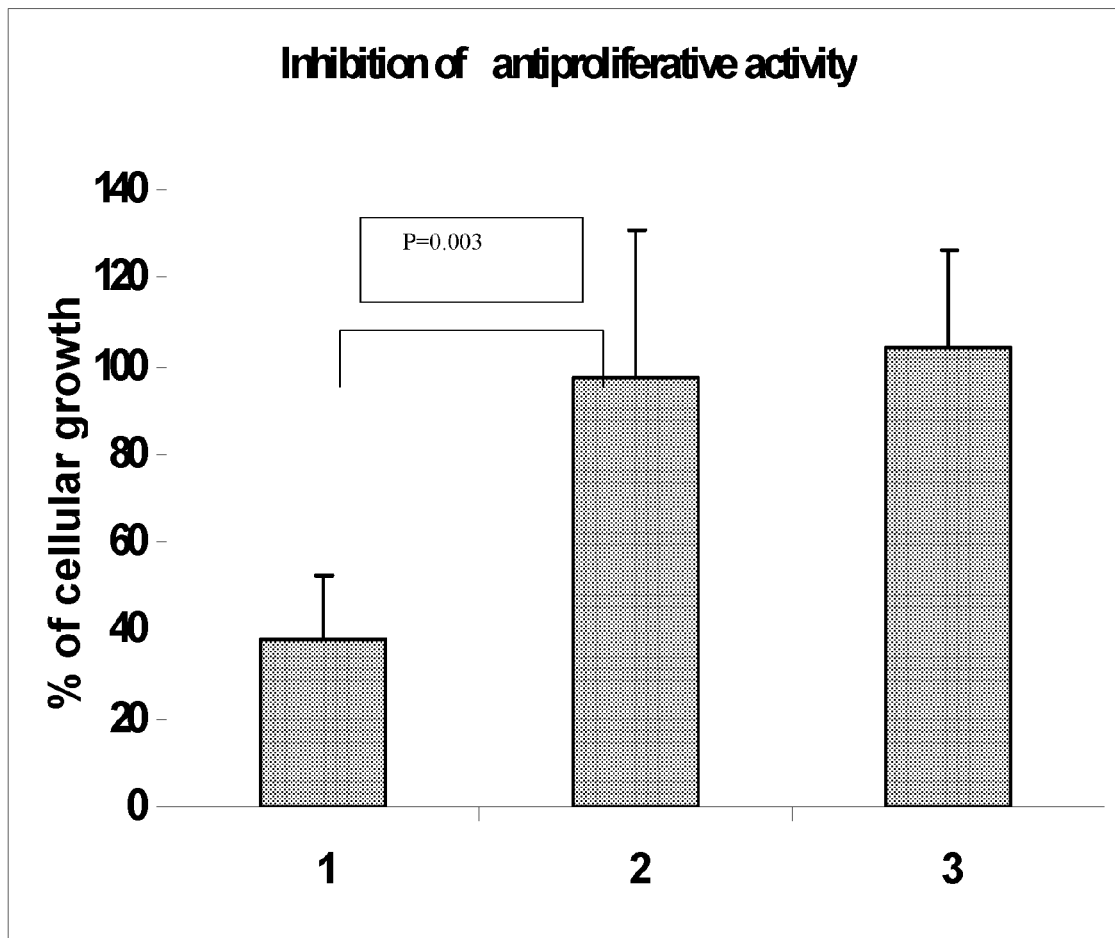

The growth of $2.5\times10^3$ cells/well of Hep-2 cultured in a MEM CANE medium (essential minimum medium with non-essential amino acids) supplemented with 10% bovine fetal serum took place in 96 well plates. They were incubated for 24 hours at 37° C. in an incubator with 5% of $CO_2$. After this time the medium was changed and the samples to be evaluated were added in serial dilutions as well as their respective controls. After 72 hours of incubation the cells were stained with 0.5% crystal violet for 2 minutes and the plates were read in a plate reader. (See FIG. 8).

Example 10

Inhibition of the induction by IFN γ of HLA II by the recombinant chimeric protein AnTH1.

Figure 9:
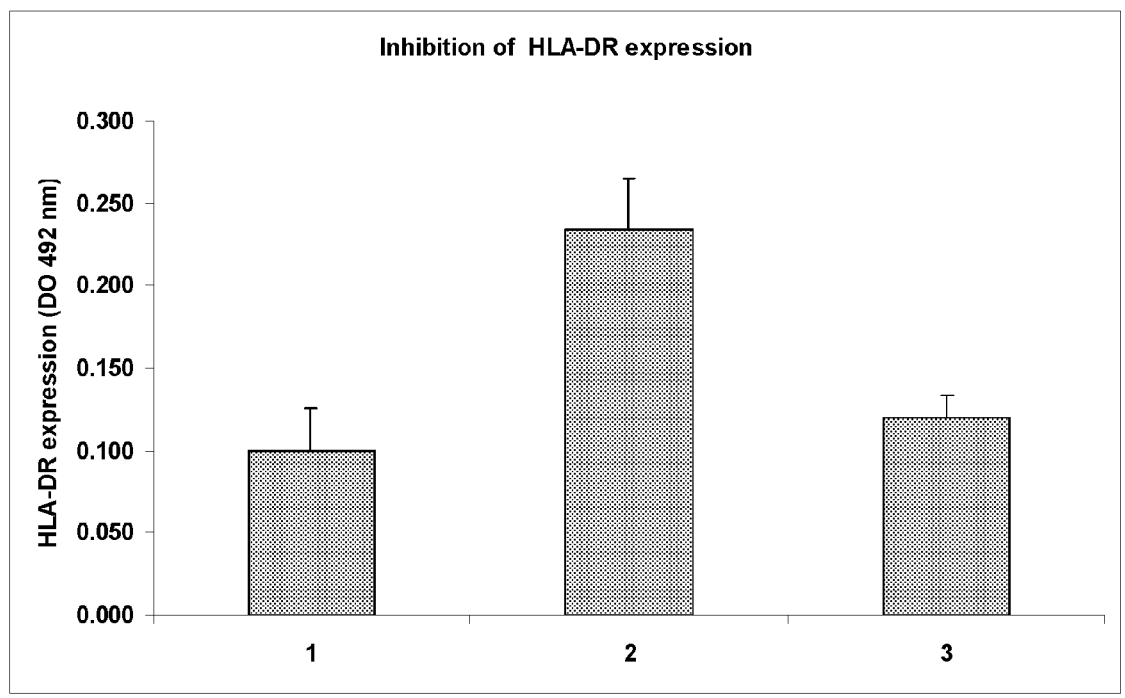

This is an ELISA trial on cells described by Seeling G. et al. *Development of receptor peptide antagonist to human γ-interferon and characterization of its ligand-bound conformation using transferred nuclear overhauser effect spectroscopy. J. Biol. Chem.* 270, 9241-53, 1995. A cell line Colo 205 was used. They were grown in culture plates with 96 wells, $2.5\times10^5$ cells/well in 0.1 mL of RPMI 1640 enriched with 10% bovine fetal serum. The cells were incubated for 12 hours at 37° C. in an incubator with a 5% $CO_2$ atmosphere. Then the cells grown in the culture medium were added in the presence of the recombinant chimeric protein and of γ IFN in a volume of 0.1 mL and then incubated for 1 hour at 37° C. After incubation, the medium was removed and the wells were washed 3 times with the culture medium. Afterwards, aliquots of 1.2 mL of the medium were added to the wells and the plates were incubated for 48 hours at 37° C. to allow for the induction of the HLA-DR antigens. The wells were washed with PBS and the cells were fixed with pure ethanol for 2 minutes. Washing was repeated and the plates were incubated for 1 hour at room temperature with a mouse monoclonal antibody anti-HLA-DR diluted in PBS 0.5% of bovine serum albumin. The wells were washed with PBS and incubated under the same conditions with the conjugate anti-IgG mouse-peroxidase. The washings were repeated 3 times and developed by adding 100 µL/well of 0.15% $H_2O_2$+5 mg/mL o-phenylendiamine. The detection of the reaction was performed with 50 µL/well of 2 M $H_2SO_4$ and absorbance was measured at 492 nm in the plate reader. (FIG. 9).

Example 11

Mass Spectrometric Analysis

An aliquot (0.5 µg) of the purified protein was analyzed by SDS-PAGE and reversed-stained with Zn-immidazol (Castellanos-Serra L, y cols. *Detection of biomolecules in electrophoresis gels with salts of imidazole and zinc II. a decade of research. Electrophoresis.* 2001, 22, 864-7). The band was excised and incubated with a citric acid solution (1%) during 5 minutes until complete colorless and incubated another 10 minutes in water to remove the excess of chelating agent. The transparent band was additionally cut in small cubes of 1 mm³ approximately, and dehydrated in a 90% acetonitrile aqueous solution with no TFA and completely dried in speed-vac. The gels pieces were rehydrated in 20-30 µL of a 50 mM $NH_4HCO_3$ solution containing 12.5 ng of a modified trypsin, sequencing grade from Promega (MA, USA). The in-gel digestion was incubated overnight at 37° C. in a termomixer (Eppendorf, USA). Additional 20 µL of 50 mM $NH_4HCO_3$ solution were added and additional 45 min were incubated and the tryptic peptides were extracted by using ZipTips C18 from Millipore (USA) previously activated and equilibrated as recommended by the manufacturer. Twenty loading cycles were carried out for extracting the tryptic peptides. The digest was acidified with formic acid, incubated 45 minutes at room temperature and another twenty loading cycles were achieved. The Ziptips were washed extensively by using a 5% formic acid solution and the proteolytic peptides were eluted in 2 µL of 60% acetonitrile containing 1% of formic acid.

The low-energy MS/MS spectra were acquired using a hybrid quadrupole orthogonal acceleration tandem mass spectrometer QTOF from Micromass (Manchester, UK) fitted with a Z-spray nanoflow electrospray ion source. The mass spectrometer was operated with a source at 80° C. and a drying gas flow of 50 L/h. Peptides were dissolved to reach an approximate concentration of 5 pmole/µL. Two microliters of the tryptic peptides were loaded onto the borosilicate nanoflow tip and 900 V and 35 V potential were applied to the nanoflow tip and entrance cone, respectively. To acquire the MS/MS spectra was used the method described by González, L. y cols. *Differentiating alpha- and beta-aspartic acids by electrospray ionization and low-energy tandem mass spectrometry. Rapid. Commun. Mass Spectrom.* 2000, 14, 2092-210. The first quadrupole was used to select the precursor ion within a window of 4-5 Th. A pressure of $\sim 3\times10^{-2}$ Pa collision gas (argon) was used in the hexapole collision cell to yield the fragment ions. Appropriate collision energy was used to reduce the intensity of the precursor ion to more than half of its original intensity. Data acquisition and processing were performed using a MassLynx system (v 3.5) from Micromass.

| ESI-MS analysis of the tryptic peptides derived from the AnTh1 protein | | | | |
|---|---|---|---|---|
| # | Peptidic sequence [a] | m/z exp. | m/z teor. | Z [b] | Abs. Error [c] |
| 1 | $^{11}$T-K$^{33}$ [d] | 908.8 | 908.83 | 3 | 0.02 |
| 2 | $^{40}$M-K$^{44}$ | 639.3 | 639.35 | 1 | 0.01 |
| 3 | $^{45}$F-K$^{50}$ | 685.3 | 685.33 | 1 | 0.00 |
| 4 | $^{56}$H-R$^{66}$ [f] | 442.8 | 442.88 | 3 | 0.01 |
| 5 | $^{67}$A-K$^{114}$ | 1781. | 1781.54 | 3 | 0.02 |
| 6 | $^{101}$Q-K$^{114}$ [d], [e] | 807.9 | 807.95 | 2 | 0.02 |
| 7 | $^{120}$N-R$^{151}$ [f] | 921.1 | 921.17 | 4 | 0.03 |
| 8 | $^{166}$S-R$^{173}$ | 506.2 | 506.23 | 2 | 0.00 |
| 9 | $^{177}$I-K$^{181}$ | 511.3 | 511.28 | 1 | 0.03 |
| 10 | $^{190}$Q-R$^{220}$ [f] | 1225. | 1225.23 | 3 | 0.03 |
| 11 | $^{221}$V-R$^{227}$ [d] | 456.7 | 456.75 | 2 | 0.01 |
| 12 | $^{228}$M-K$^{236}$ [d] | 535.2 | 535.25 | 2 | 0.01 |

[a] The numbering in the sequences of peptides is according to the AnTh1 protein shown in FIG. 10 (SEQ ID NO:9)
[b] Charge state of the individual peptides.
[c] Indicate the absolute mass difference between the theoretical and experimental molecular masses of the detected peptides.
[d] Peptides sequenced by ESI-MS/MS.
[e] Peptide originated by the non-specific cleavage of trypsin.
[f] Peptide containing free cysteine Advantages of the Proposed Solution.

The invention combines in one molecule the ability to intervene in two signaliation systems affecting immuno-regulating and inflammatory mechanisms. The design of the chimeric protein consists of the fusion of a ligand (IL-2$_{60}$) through a 4 amino acid peptide with an extra-cellular receptor (Rα IFN γ). This combination allows the binding of the recombinant chimeric protein with the cells containing on their surface the Rα IL-2. This subunit is mainly present in non-activated T cells and in the high affinity IL-2 receptor (Rαβγ IL-2) in the activated T cells (Smith, K. A. *The interleukin-2 receptor. Annu. Rev. Cell. Biol.* 5, 397-403, 1989 and Strom, T. B. et al. *Interleukin-2 receptor-directed therapies: antibody-or cytokine-based targeting molecules. Annu. Rev. Med.* 44, 343-50, 1993).

If the AnTH1 protein binds to the RαIL-2 in the cells at rest, it can internalize the protein, leaving Rα IFN γs in the cytoplasm under the conditions of being recycled outwards and interfering with the γ IFN that will be produced on activating the cells. The interaction of the γ IFN from the cytoplasm with an intracellular region of the membrane receptor that may generate the biological activity of γ IFN, has been described (Szente B. E. et al. *Identification of IFN (receptor binding sites for JAK2 and enhancement of binding by IFN γ and its C-terminal peptide IFN γ (95-133). J. Immunol.* 155, 5617-22, 1995). During a disease where there may be a need of decreasing the action of the IL-2 produced by the body when adding the AnTH1 protein, this will bind through the IL-2$_{60}$ portion to the alpha subunit in the high affinity complex (Rαβγ IL-2) in the activated cells, it will interfere with the binding of the complete IL-2 (native) secreted by the cells of the immune system and will interfere in its biological activity. On the other hand the γ IFN that has already been secreted by the activated T cells can be sequestered by the Rα IFN γs portion of the chimeric protein, avoiding its attachment to the membrane receptor. In this way, an autoimmune, and/or inflammatory reaction can be controlled in two different moments, during the activation and in the process of propagating the reaction.

The invention offers a hetero-bivalent chimeric protein that may interfere with the biological activity of the IL-2 and the γ IFN. Considering that the recombinant chimeric protein AnTH1 also has a T cell growth stimulating activity, a less profound inactivation of the immune system may be expected, which will provoke antagonist anticytokines that were already clinically proven.

What is claimed is:

1. A recombinant chimeric protein comprising the amino acid sequence set forth in SEQ ID NO: 9.

2. A pharmaceutical composition comprising an effective amount of a recombinant chimeric protein, wherein the protein comprises the amino acid sequence set forth in SEQ ID NO: 9.

* * * * *

UNITED STATES PATENT AND TRADEMARK OFFICE
CERTIFICATE OF CORRECTION

PATENT NO. : 7,429,384 B2
APPLICATION NO. : 10/513931
DATED : September 30, 2008
INVENTOR(S) : Rivero et al.

It is certified that error appears in the above-identified patent and that said Letters Patent is hereby corrected as shown below:

ON THE TITLE PAGE Item [74]:

Now reads: "Hoffman"

Should read: -- Hoffmann --

IN THE PATENT:

Column 2, line 1:

Now reads: "IL-10, I"

Should read: -- IL-10, IL-4 --

Column 4, line 9:

Now reads: "Desig"

Should read: -- Design --

Column 5, line 17:

Now reads: "hihg-affinity"

Should read: -- high-affinity --

Column 7, line 47:

Now reads: "monolonal"

Should read: -- monoclonal --

UNITED STATES PATENT AND TRADEMARK OFFICE
CERTIFICATE OF CORRECTION

PATENT NO.        : 7,429,384 B2
APPLICATION NO.   : 10/513931
DATED             : September 30, 2008
INVENTOR(S)       : Rivero et al.

It is certified that error appears in the above-identified patent and that said Letters Patent is hereby corrected as shown below:

Column 9, line 60:

Now reads: "HLA-II bγ"

Should read: -- HLA-II b<u>y</u> --

Column 15, line 52:

Now reads: "induction bγ"

Should read: -- induction b<u>y</u> --

Signed and Sealed this

Thirty-first Day of March, 2009

JOHN DOLL
*Acting Director of the United States Patent and Trademark Office*

SEQUENCE LISTING

<160> NUMBER OF SEQ ID NOS: 9

<210> SEQ ID NO 1
<211> LENGTH: 30
<212> TYPE: DNA
<213> ORGANISM: Homo sapiens

<400> SEQUENCE: 1
ccatggcacc tactttcaag ttctacaaag          30

<210> SEQ ID NO 2
<211> LENGTH: 32
<212> TYPE: DNA
<213> ORGANISM: Homo sapiens

<400> SEQUENCE: 2
catcatatgg gtctagacac tgaagatgtt tc          32

<210> SEQ ID NO 3
<211> LENGTH: 29
<212> TYPE: DNA
<213> ORGANISM: Homo sapiens

<400> SEQUENCE: 3
cccatatgat gagcagggct gagatgggc          29

```
<210> SEQ ID NO 4
<211> LENGTH: 31
<212> TYPE: DNA
<213> ORGANISM: Homo sapiens

<400> SEQUENCE: 4
ggatccttat tttatactgc tattgaaaat g                              31

<210> SEQ ID NO 5
<211> LENGTH: 193
<212> TYPE: DNA
<213> ORGANISM: Homo sapiens

<400> SEQUENCE: 5
atggcaccta cttcaagttc tacaaagaaa acacagctac aactggagca tttactgctg    60
gatttacaga tgattttgaa tggaattaat aattacaaga atcccaaact caccaggatg   120
ctcacattta agttttacat gcccaagaag gccacagaac tgaaacatct tcagtgtcta   180
gacccatatg atg                                                     193

<210> SEQ ID NO 6
<211> LENGTH: 11
<212> TYPE: DNA
<213> ORGANISM: Homo sapiens

<400> SEQUENCE: 6
cccatatgat g                                                        11

<210> SEQ ID NO 7
<211> LENGTH: 703
<212> TYPE: DNA
<213> ORGANISM: Homo sapiens

<400> SEQUENCE: 7
cccatatgat gagcagggct gagatgggca ccgcggatct ggggccgtcc tcagtgccta    60
caccaactaa tgttacaatt gaatcctata acatgaaccc tatcgtatat tgggagtacc   120
agatcatgcc acaggtccct gttttttaccg tagaggtaaa gaactatggt gttaagaatt   180
cagaatggat tgatgcctgc atcaatattt ctcatcatta ttgtaatatt tctgatcatg   240
ttggtgatcc atcaaattct cttttgggtca gagttaaagc cagggttgga caaaaagaat   300
ctgcctatgc aaagtcagaa gaatttgctg tatgccgaga tggaaaaatt ggaccaccta   360
aactggatat cagaaaggag gagaagcaat catgattgac atatttcacc cttcagtttt   420
tgtaaatgga gacgagcagg aagtcgatta tgatcccgaa actacctgtt acattagggt   480
gtacaatgtg tatgtgagaa tgaacggaag tgagatccga tataaatac tcacgcagaa    540 ggaagatgat tgtgacgaga ttcagtgcca gttagcgatt ccagtatcct cactgaattc   600
tcagtactgt gtttcagcag aaggagtctt acatgtgtgg ggtgttacaa ctgaaaagtc   660
aaaagaagtt tgtattacca ttttcaatag cagtataaaa taa                    703

<210> SEQ ID NO 8
<211> LENGTH: 885
<212> TYPE: DNA
<213> ORGANISM: Homo sapiens

<400> SEQUENCE: 8
atggcaccta cttcaagttc tacaaagaaa acacagctac aactggagca tttactgctg    60
gatttacaga tgattttgaa tggaattaat aattacaaga atcccaaact caccaggatg   120
```
ctcacattta agttttacat gcccaagaag gccacagaac tgaaacatct tcagtgtcta    180
gacccatatg atgagcaggg ctgagatggg caccgcggat ctggggccgt cctcagtgcc    240
tacaccaact aatgttacaa ttgaatccta taacatgaac cctatcgtat attgggagta    300
ccagatcatg ccacaggtcc ctgttttac cgtagaggta agaactatg gtgttaagaa    360 ttcagaatgg attgatgcct gcatcaatat ttctcatcat tattgtaata tttctgatca    420
tgttggtgat ccatcaaatt ctctttgggt cagagttaaa gccagggttg acaaaaaga    480 atctgcctat gcaaagtcag aagaatttgc tgtatgccga gatggaaaaa ttggaccacc    540
taaactggat atcagaaagg aggagaagca atcatgattg acatatttca cccttcagtt    600
tttgtaaatg gagacgagca ggaagtcgat tatgatcccg aaactacctg ttacattagg    660
gtgtacaatg tgtatgtgag aatgaacgga agtgagatcc agtataaaat actcacgcag    720
aaggaagatg attgtgacga gattcagtgc cagttagcga ttccagtatc ctcactgaat    780
tctcagtact gtgtttcagc agaaggagtc ttacatgtgt ggggtgttac aactgaaaag    840
tcaaaagaag tttgtattac cattttcaat agcagtataa aataa                   885

<210> SEQ ID NO 9
<211> LENGTH: 294
<212> TYPE: PRT
<213> ORGANISM: Homo sapiens

<400> SEQUENCE: 9

Ser Ala Pro Thr Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Ala His Met Met
    50                  55                  60

Ser Arg Ala Glu Met Gly Thr Ala Asp Leu Gly Pro Ser Ser Val Pro
65                  70                  75                  80

Thr Pro Thr Asn Val Thr Ile Glu Ser Tyr Asn Met Asn Pro Ile Val
                85                  90                  95

Tyr Trp Glu Tyr Gln Ile Met Pro Gln Val Pro Val Phe Thr Val Glu
            100                 105                 110

Val Lys Asn Tyr Gly Val Lys Asn Ser Glu Trp Ile Asp Ala Cys Ile
        115                 120                 125

Asn Ile Ser His His Tyr Cys Asn Ile Ser Asp His Val Gly Asp Pro
    130                 135                 140

Ser Asn Ser Trp Val Arg Val Lys Ala Arg Val Gly Gln Lys Glu Ser
145                 150                 155                 160

Ala Tyr Ala Lys Ser Glu Glu Phe Ala Val Cys Arg Asp Gly Lys Ile
                165                 170                 175

Gly Pro Pro Lys Leu Asp Ile Arg Lys Glu Glu Lys Gln Ile Met Ile
            180                 185                 190

Asp Ile Phe His Pro Ser Val Phe Val Asn Gly Asp Glu Gln Glu Val
        195                 200                 205

Asp Tyr Asp Pro Glu Thr Thr Cys Tyr Ile Arg Val Tyr Asn Val Tyr
    210                 215                 220

Val Arg Met Asn Gly Ser Glu Ile Gln Tyr Lys Ile Leu Thr Gln Lys
225                 230                 235                 240

-continued

```
Glu Asp Asp Cys Asp Glu Ile Gln Cys Gln Leu Ala Ile Pro Val Ser
            245                 250                 255

Ser Leu Asn Ser Gln Tyr Cys Val Ser Ala Glu Gly Val Leu His Val
            260                 265                 270

Trp Gly Val Thr Thr Glu Lys Ser Lys Glu Val Cys Ile Thr Ile Phe
            275                 280                 285

Asn Ser Ser Ile Lys Gly
            290
```